(12) United States Patent
Bell et al.

(10) Patent No.: US 6,517,522 B1
(45) Date of Patent: Feb. 11, 2003

(54) TUBULAR INTRAVENOUS SET

(75) Inventors: David Bell, Grayslake, IL (US); William J. Schnell, Libertyville, IL (US); David S. Utterberg, Seattle, WA (US)

(73) Assignee: DSU Medical Corporation, Las Vegas, NV (US)

( * ) Notice: Subject to any disclaimer, the term of this patent is extended or adjusted under 35 U.S.C. 154(b) by 0 days.

(21) Appl. No.: 09/541,282

(22) Filed: Apr. 3, 2000

(51) Int. Cl.⁷ .............................................. A61M 5/00
(52) U.S. Cl. .............. 604/263; 604/165.03; 604/165.02
(58) Field of Search ................................ 604/263, 154, 604/164.01, 164.12, 165.02, 165.03, 160, 161

(56) References Cited

U.S. PATENT DOCUMENTS

| | | | |
|---|---|---|---|
| 3,537,451 A | * 11/1970 | Murray et al. | 604/165.03 |
| 4,627,842 A | * 12/1986 | Katz | 604/177 |
| 4,941,881 A | 7/1990 | Masters et al. | 604/162 |
| 5,000,740 A | * 3/1991 | Ducharme et al. | 604/162 |
| 5,112,311 A | 5/1992 | Utterberg | 604/177 |
| 5,238,010 A | * 8/1993 | Grabenkort et al. | 128/846 |
| 5,279,590 A | * 1/1994 | Sinko et al. | 604/162 |
| 5,290,264 A | 3/1994 | Utterberg | 604/263 |
| 5,312,359 A | * 5/1994 | Wallace | 604/164.08 |
| 5,334,149 A | * 8/1994 | Nortman et al. | 604/263 |
| 5,411,480 A | * 5/1995 | Kriesel | 604/153 |
| 5,413,562 A | * 5/1995 | Swauger | 604/179 |
| 5,489,273 A | * 2/1996 | Whitney et al. | 604/161 |
| 5,498,241 A | * 3/1996 | Fabozzi | 604/165.03 |
| 5,562,636 A | 10/1996 | Utterberg | 604/263 |
| 5,562,637 A | 10/1996 | Utterberg | 604/263 |
| 5,695,476 A | * 12/1997 | Harris | 604/192 |
| 5,704,917 A | 1/1998 | Utterberg | 604/180 |
| 5,704,924 A | 1/1998 | Utterberg et al. | 604/263 |
| 5,772,638 A | 6/1998 | Utterberg et al. | 604/263 |
| 5,810,775 A | * 9/1998 | Shaw | 604/195 |
| 5,827,239 A | 10/1998 | Dillon et al. | 604/263 |
| 5,833,570 A | 11/1998 | Dillon et al. | 604/263 |
| 5,951,529 A | 9/1999 | Utterberg | 604/263 |
| 6,042,570 A | 3/2000 | Bell et al. | 604/192 |
| 6,186,325 B1 | * 2/2001 | Schmidt et al. | 206/364 |

FOREIGN PATENT DOCUMENTS

| | | | |
|---|---|---|---|
| EP | 0409057 A1 | * | 11/1990 |
| FR | 2620341 A1 | * | 3/1989 |
| WO | WO-91/00116 | * | 1/1991 |

* cited by examiner

*Primary Examiner*—Edward K. Look
*Assistant Examiner*—Dwayne White
(74) *Attorney, Agent, or Firm*—Garrettson Ellis Seyfarth Shaw

(57) ABSTRACT

A medical needle protector sheath comprises a tubular body for surrounding and shielding a needle with the sheath defining an anchor member integrally attached to the front of the body for manual holding, plus a closure cap for the front end which is integrally attached to the body. Also, a manually removable wing member may be carried about the hub of the needle. A tunnel member typically of the inverted U-cross section provides longitudinal securance to the needle and hub while penetrating the skin of the patient while at the same time permitting axial rotation of the needle.

11 Claims, 2 Drawing Sheets

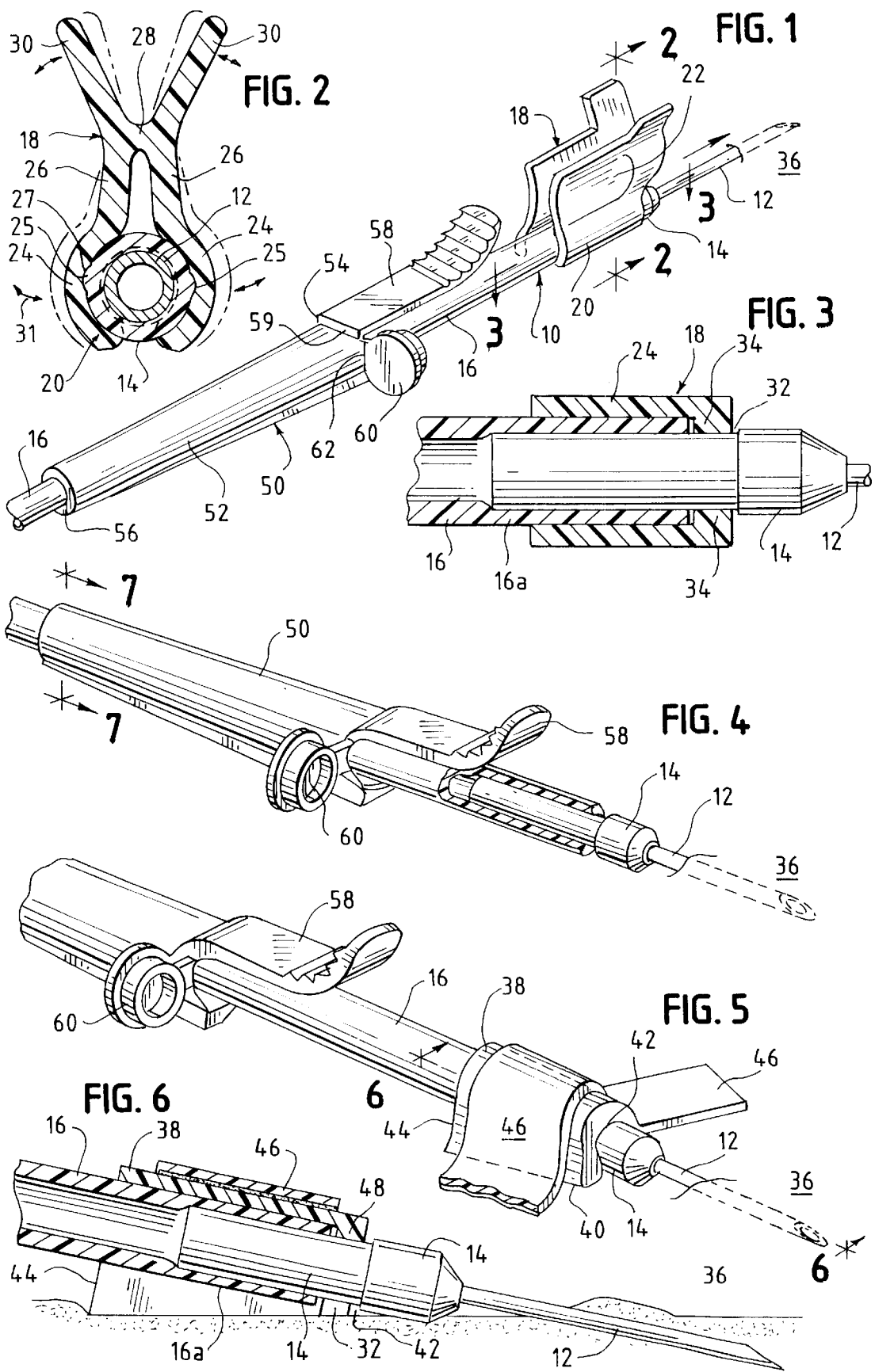

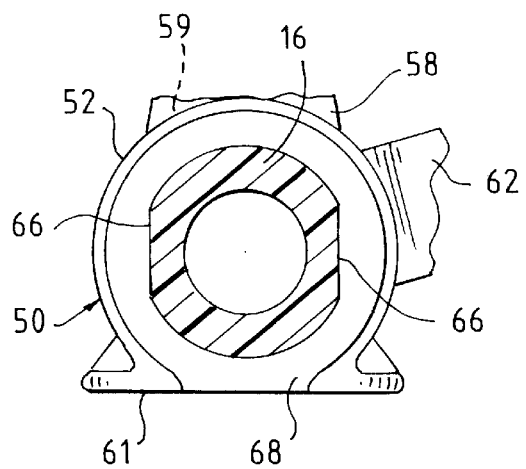
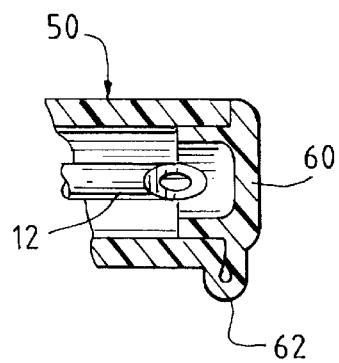
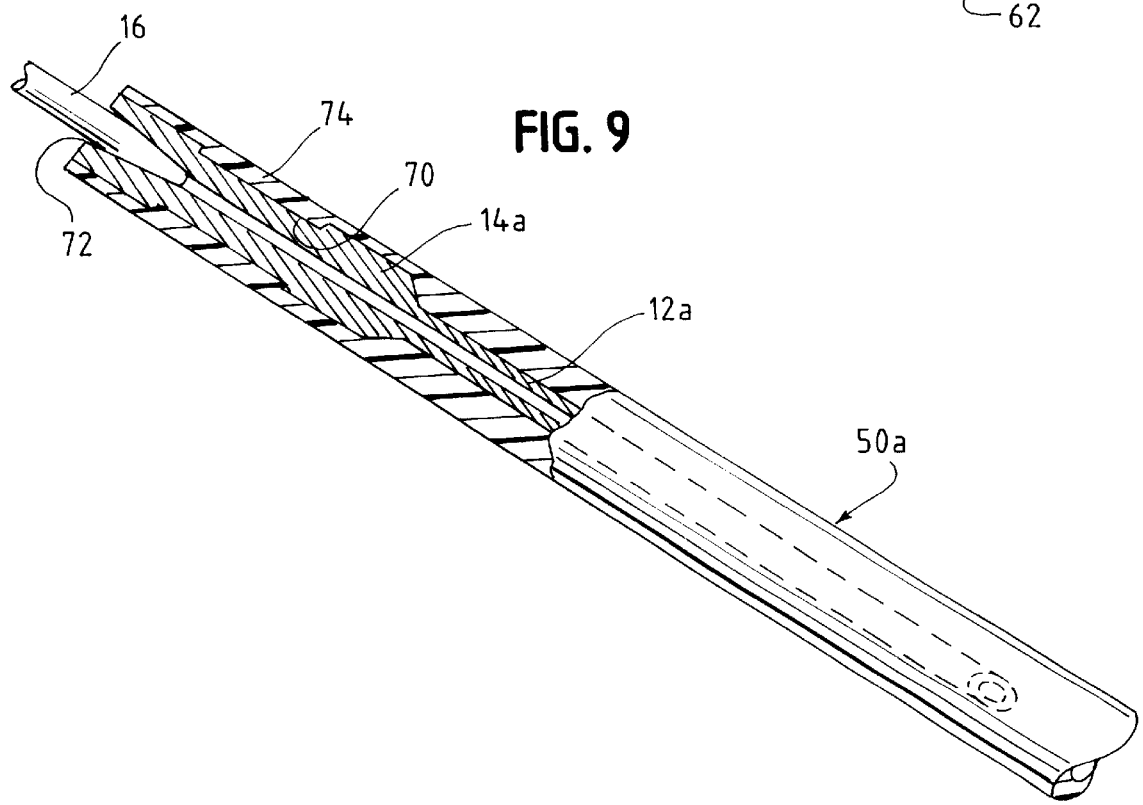

TUBULAR INTRAVENOUS SET

BACKGROUND OF THE INVENTION

The invention relates to a tubular intravenous set having various improvements. Such sets are commonly used to gain access to the vascular system of the patient for purposes of blood access for extracorporeal blood processing such as hemodialysis, or for the administration of parenteral solutions, blood, or other medical solutions to the patient.

In the prior art sets for intravenous access to a patient, a medical needle is attached to typically a winged hub, which hub, in turn, is attached to the flexible tubing of the set. The wings of the hub are flexible, being generally folded up, to be gripped by the fingers as the needle is inserted into the vascular system. Then, the wings are folded down and taped to the skin to retain the needle in position.

However, certain drawbacks exist with this system despite its widespread clinical use. For example, if the needle enters the vascular system at an angle that is slightly steeper than normal, the patient may experience discomfort when the wings of the hub are taped down, in that such taping will tend to rotate the needle tip upwardly, resulting in chronic discomfort and even damage to the vein wall while the needle remains in position. Also, the wings are flexible, causing an uncertainty in the process of needle insertion resulting from an absence of rigidity as the wings are gripped.

By this invention, a substantially rigid wing system for the needle hub is provided, which improves the ability of the technician to make an effective and proper entry of the needle into the vascular system. Then, by this invention, the wing member can be removed after the needle has been emplaced, and the needle hub may be taped in position. Alternatively, this invention provides a securance system of the needle hub to the skin in which an angular variation of the needle and hub may be permitted and protected by a rigid system, so that the tip of the needle within the blood vessel is not urged by taping of the hub to the skin into an angular direction that can cause discomfort to the patient and even blood vessel damage.

Additionally, this invention relates to a new design of needle protector sheath for use with preferably wingless needle hubs, in which, after use, the needle can be retracted from the vascular system of a patient, withdrawing into the sheath of this invention so that the sharp tip of the needle is enclosed in the sheath to eliminate the possibility of accidental needle sticks. In the large body of prior art, among others, see Utterberg et al. U.S. Pat. No. 5,112,311; Utterberg U.S. Pat. Nos. 5,562,637; 5,290,264; 5,562,636; 5,951,529; 5,704,917; and Utterberg et al. U.S. Pat. Nos. 5,704,924 and 5,772,638. These patents all disclose needle protector sheaths for use with winged needles, with the sheaths carrying slots through which the wings project.

DESCRIPTION OF THE INVENTION

In accordance with this invention a tubular medical needle set is provided which comprises: a needle and needle hub connected to an end of flexible tubing plus a wing member positioned to facilitate manual gripping of the needle and hub, either by gripping the hub directly or by gripping flexible tubing which is positioned outside of the hub.

The wing member comprises a hub gripping portion (which may grip the tubing adjacent to the hub), and a wall portion attached to the hub gripping portion. The wall portion extends laterally outwardly from the hub gripping portion for manual gripping as the needle is being manipulated. The hub gripping portion is manually disengageable from the hub, for manual removal of the wing member after the needle has been emplaced in a patient. Then, the needle may be directly taped, or may be placed in a tunnel member, which is described below along with the advantages thereof.

Preferably, the wing member comprises a pair of walls and attached hub gripping members which grip the hub, each attached hub gripping member being respectively positioned on an opposed side of the hub to the other hub gripping member. The pair of walls extend in generally parallel, adjacent manner laterally outwardly from the hub, each extending from one of the hub gripping members. The pair of walls define the wall portion described above.

The walls are integrally attached together by a hinge wall. The walls also each define a squeeze portion extending laterally outwardly beyond the hinge wall. Thus, manual squeezing of the squeeze portion disengages the hub gripping members from the hub, to permit removal of the wing member. The hinge wall flexes to an extent, but is biased to force the hub gripping members into their gripping relation.

Preferably, a groove may extend around the needle hub. The hub gripping members may define projections that fit in the groove, to restrict axial sliding of the wing member while gripping the hub. Typically, the groove is defined between the hub and the connected, flexible tubing end carried on the hub.

The wing member may be substantially rigid when mounted on the hub, to be manually gripped as the needle is used in a phlebotomy procedure to enter a blood vessel of the patient. Then, the wing member may be removed. A substantially rigid tunnel member may be applied to enclose at least a portion of the hub resting on the skin of the patient. The tunnel member has a cross section of substantially the shape of an inverted U, to define two tunnel edges for resting on the skin of a patient, while the needle of the enclosed needle hub penetrates the patient's skin.

The tunnel member may have front and rear apertures through which the hub and tubing extend. The rear aperture may be larger than the front aperture, to accommodate a range of angular needle positions in the tunnel member. The tunnel member provides protection and retention to the needle hub, while having a tolerance for a variation in the angle of penetration of the needle through the skin.

The tunnel member may be secured to the skin of a patient by a strip of medical tape, thus securing the needle and hub in position, while permitting the needle and hub to rotate if desired, and protecting the needle and hub even if there is a variation of angle of entrance into the skin, without biasing or otherwise forcing the needle tip to move in an undesirable direction.

To secure the needle and hub longitudinally in position, the front aperture of the tunnel member may at least in part be defined by a front, inwardly extending flange. A groove is defined in the hub, typically the same groove that is engaged by the wing member which may have been previously removed. This groove receives the front flange of the tunnel member, and thus prevents longitudinal movement between the tunnel member and the needle hub. Accordingly, protection of the needle and hub is provided by the tunnel member, while permitting rotatability of the needle and hub about the needle axis, and with tolerance of a variety of needle entrance angles of the needle to the vascular system relative to the skin of the patient.

Further in accordance with this invention, a medical needle protector sheath is provided, which comprises a tubular body for surrounding and shielding a needle. The body has front and rear ends, with the sheath defining a substantially flat anchor member, which is integrally attached to a first attachment portion of the front end of the body, and extends forwardly from the front end of the body, to be manually held to retain the protector sheath from movement as the needle is being withdrawn from the skin of a patient into the tubular body. This has similarity to that which is described in the previously cited Utterberg et al. U.S. Pat. No. 5,112,311 and Utterberg U.S. Pat. Nos. 5,562,637 and 5,772,638.

Additionally, the protector sheath of this invention carries a closure cap for the front end. The cap is also integrally attached to the tubular body. Specifically, the closure cap may be integrally attached to another portion of the front end of the body through a hinged connector member, so that the closure cap may be moved by hinge action to close after the tip of the needle has been retracted into the protector sheath, upon withdrawal of the needle from the patient. The needle tip is more reliably enclosed and may be effectively sealed, particularly in slot-free sheath designs, with the closure cap being preferably thick enough so that the needle cannot penetrate through it. Thus blood drops do not leak from the sheath. Also, the present sheath may be smaller in diameter than corresponding slotted designs.

The closure cap may specifically be attached to the front end of the body at an end portion which forms about a 40 to 140 degree angle to the area of the first attachment portion of the anchor member at the front end. Thus, the closure cap closes in a transverse direction relative to the transverse direction which the anchor member moves when held or pressed downwardly with the finger, for retaining the protector sheath as the needle is withdrawn from the patient into the sheath.

The rear end of the protector sheath may carry at least one gripper to retain the sheath in position surrounding and shielding the needle. The gripper may comprise at least a pair of spaced flanges that engage tubing surrounding the needle hub. The flanges may be diametrically spaced, straight inner edge portions of a ring-shaped flange member.

As is common with respect to the protector sheaths for winged needles, the sheath may initially reside on a length of the set tubing which is spaced from the needle and hub. Then, when it is desired to withdraw the needle from the patient, the sheath may be moved forward along the set tubing. Before the sheath gets to the vicinity of the needle hub, the two diametrically spaced, straight inner edge portions of the flange, which are of reduced distance from each other relative to the remaining inner diameter of the protector sheath, compress the set tubing slightly in one dimension, causing it to assume a slightly oval shape. This permits easy sliding of the sheath along the tubing. However, when the sheath and its flange member at the back arrive at the needle hub, with the set tubing surrounding the needle hub, the tubing can no longer be pushed into an oval configuration because of the inner radial support of the needle hub. Therefore, the straight inner edge portions of the ring-shaped flange member bite into the soft tubing and become fixed in position, so that the sheath is no longer easily withdrawn.

Alternatively, the protector sheath of this invention may have a gripper which comprises an inwardly extending projection to engage a recess in the needle hub, in typically a snap-fit retention for retaining the protector sheath in an advanced position on the needle hub and enclosing the point of the needle.

The tubular body of the protector sheath may be substantially cylindrical, with optionally a flat, external surface portion defined along one side thereof. The one side is typically positioned in circumferentially opposed relation to the first portion of the front end of the body that connects with the anchor. Thus, a flat surface is provided upon which the sheath rests against the skin or a bandage over the skin. The added, integral front end closure of the protector sheath is desirable for avoiding any spillage of blood after withdrawal of the needle from the patient. This closure is provided in conjunction with the anchor, which greatly facilitates the safe withdrawal of the needle and its entry into the protector sheath.

While the protector sheath of this invention is illustrated as being free of slots, it may also have slots if desired, to accommodate needles having winged hubs for the safe storage of the needle tips.

Thus, a tubular, intravenous set is provided in which a rigid wing on the hub gives improved ability for an optimum phlebotomy with the needle, when compared with the flexible wings which are gripped in the prior art winged needles. The wing member of this invention may then be removed to permit taping down as desired. As a preferred alternative, a tunnel member is provided to permit taping and retention of the needle in position without bending the needle out of its natural angle of approach to the skin, and also permitting the needle and hub to be axially rotated if needed.

The wing member of this invention can be attached to conventional wigless needle hubs to provide them with the advantages of a rigid wing.

Furthermore, a protector sheath is provided for the needle tip which carries the desired anchor at its front end, and also a hinged front end closure to seal the front end of the protector sheath after the needle has been safely stored inside.

DESCRIPTION OF THE DRAWINGS

In the drawings,

FIG. 1 is a back perspective view of a medical needle and needle hub set, connected to an end of flexible tubing, incorporating the invention of this application;

FIG. 2 is a sectional view taken along line 2—2 of FIG. 1;

FIG. 3 is a sectional view taken along line 3—3 of FIG. 1;

FIG. 4 is a front perspective view of the needle set of FIG. 1 emplaced within the skin of a patient and showing the front of the protector sheath carried thereon, and with the removable wing member taken away;

FIG. 5 is a front perspective view showing the needle set of this invention emplaced within the skin of a patient and utilizing the tunnel member of this invention;

FIG. 6 is a sectional view taken along line 6—6 of FIG. 5;

FIG. 7 is an enlarged, elevational, rear end view of the protector sheath shown in the previous drawings;

FIG. 8 is a fragmentary, longitudinal sectional view of the front end of the protector sheath, the view shown rotated 90 degrees and advanced into its needle-enclosing position; and FIG. 9 is a fragmentary, partially longitudinal sectional view of another design of the needle and hub set usable in this invention, showing it to be enclosed with another embodiment of the protector sheath of this invention.

DESCRIPTION OF THE SPECIFIC EMBODIMENTS

Referring to the drawings, tubular medical needle set 10 comprises a needle 12, needle hub 14, and flexible set tubing 16 which is secured on needle hub 14 in conventional manner.

In accordance with this invention, needle set 10 may carry a wing member 18 which is positioned to manually grip hub 14, as particularly shown in FIGS. 2 and 3.

Wing member 18 comprises a hub gripping portion 20 which portion is carried by needle hub 14. Wing member 18 also comprises a wall portion 22, which is attached to the hub gripping portion 20. Wall portion 22 extends laterally outwardly from hub gripping portion 20 to permit manual gripping by the user. Thus, needle 12 can be manually controlled with ease as it is inserted into the venous system of a patient.

As can be seen particularly in FIG. 2, hub gripping portion 20 and the entire wing member 18 is manually disengageable from needle hub 14 so that the entire wing member 18 can be manually removed after needle 12 has been emplaced in the patient. As shown, this may be accomplished when hub gripping portion 20, as shown, comprises a pair of hub gripping members 24, which grip hub 14 respectively on opposed sides thereof. A pair of walls 26, which respectively comprise the wall portion 22 extend in generally parallel manner laterally outward, each from one of the hub gripping members 24. Walls 26 are integrally attached together by hinge wall 28, and each define a squeeze portion 30 extending laterally outwardly beyond hinge wall 28.

Hub 14 may define an opposed pair of projections 25 which snap fit into corresponding recesses 27 defined in the hub gripping members 24. Thus, hub 14 may be secured within wing member 18 in a bevel-up needle position which is securely rotatably maintained with respect to wing member 18 for easy cannulation into the vascular system of the patient 36. Then, wing member 18 may be removed as described above.

Thus it can be seen that wing member 18 may be made of a single piece of molded plastic having a certain degree of flexibility. Manual squeezing of squeeze portions 30 permits disengagement of hub gripping member 24 from the hub per arrows 31, to permit removal of the wing member. Wing member 18 is designed so that hub gripping members 24 are biased inwardly to be normally retained in engagement with the hub 14.

Referring to FIG. 3, it can be seen that tubing 16 and hub 14 together define an annular groove 32 into which projections 34 of the respective hub gripping members 24 can reside. Thus, axial sliding of wing member 18 is restricted in its normal hub gripping position.

Thus, the set of this invention may initially be in the configuration of FIG. 1, in which the user grips wing member 18 to pass needle 12 through the skin 36 of a patient, thus occupying the position shown in FIG. 4. Then, wing 18 may be removed as described above, as shown in FIG. 4, and a tunnel member 38 may be applied as shown in FIG. 5. Tunnel member 38 has the cross section of substantially an inverted U, defining a pair of tunnel edges 40 which rest against the skin 36. Tunnel member 38 also has front aperture 42 and rear aperture 44 through which the hub 14 and tubing 16 extend as shown in FIG. 5. Rear aperture 44 is larger than front aperture 42, to permit needle 10 occupy a range of angular needle positions in tunnel member 38 as particularly shown in FIG. 6. Needle 12 and hub 14 are occupying a near maximum vertical rotational position as shown in FIG. 6, but it would be possible for the needle to occupy a position closer to the horizontal, and to still occupy tunnel member 38 without rotational or bending stress on the needle, so that less discomfort or damage is experienced by the patient.

As shown, tunnel member 38 is secured to the skin of the patient by a strip of medical tape 46, while needle 12 penetrates the skin of the patient 36. It can be noted that the set and needle 12 can be rotated about their major axis while occupying the position of FIG. 5 and retained by tunnel 38 and tape 46, which may be desirable in some clinical circumstances. Also, needle 12 and set 10 are axially retained in tunnel member 38 by flange 48 at front end 42 of tunnel member 38, which flange fits into annular groove 32 of the set, the same annual groove that is used with wing member 18. Thus, the needle and set are firmly secured on the patient while at the same time axial rotation is permitted.

Referring again particularly to FIGS. 1, 5 and 7, flexible tubing 16 carries a protector sheath 50, which is broadly similar in function to the protector sheaths of the patents cited above, but shown here in a slotless version. Sheath 50 comprises a tubular body 52 having a front end 54 and a rear end 56. Sheath 50 defines an anchor member 58, of generally conventional design, being integrally attached by hinge 59 to the front end of body 52 and extending forwardly from the front end 54, to be manually held to retain the protector sheath as the needle is being withdrawn from the skin of a patient into the tubular body, in a manner that is known practice.

Also, a hinged closure cap 60 is provided at front end 54, being integrally attached to body 50 through hinge 62.

It can be seen that closure cap 60 is connected to front end 54 of sheath 50 by a hinge 62 which is substantially perpendicular to hinge 59 of anchor member 58, so that two members 58, 60 swing on their hinges in substantially perpendicular directions. Thus, neither will interfere with the other.

Protector sheath 50 carries a gripper to retain the sheath in position surrounding and shielding the needle. Specifically as one embodiment, FIG. 7 shows a pair of spaced flanges 66, which comprise diametrically spaced, straight inner edge portions of a ring-shaped flange member 68, which is positioned adjacent to rear end 56 of sheath 50 as previously described. Ring flange 68 and the flat edge portions 66 may be proportioned so that the tubing normally passes through the flange with ease, with the tubing deflecting slightly inwardly as it encounters straight edges 66, since the tubing has a diameter slightly greater than the spacing between edges 66. However, the tubing 16a which is carried on hub 14 has a slightly enlarged outer diameter over other tubing lengths and is resistant to inward deflection, because of the presence of hub 14. Thus, when edge portions 66 encounter tubing at this point, they bite into the soft tubing to form a secured retention, which resists retraction of sheath 50. This occurs when needle 10 has been retracted to be enclosed within sheath 50, as shown in FIG. 8, taking place upon the retraction of the needle from the skin while one retains sheath 50 by means of anchor 58. Then, one manually releases the anchor and closes cap 60, so that the needle is reliably sealed (particularly when free of slots) so that any drops of blood that leak will be retained within sheath 50, and the enclosed needle may not require disposal in a "sharps" container.

Tubular body 52 may be substantially cylindrical, with a flat, external surface portion 61, defined along the side of the cylindrical body 52, that is positioned in diametrically opposed relation to hinge 59 of the anchor 58. Thus surface portion 61 serves as flat stand on which sheath 50 can rest.

Turning to FIG. 9, another design of needle hub and needle protector sheath is shown. Needle 12a and hub 14a are shown, with the design of hub 14a being somewhat different, in that the hub defines an annular groove 70 without making use of the front end of tubing 16, as in the previous embodiment. Instead, tubing 16 may fit within a flared portion 72 of the lumen of hub 14a in a conventional manner. Sheath 50a may be of a design generally similar to that of the previous embodiment, except for a different design of gripper to retain the sheath in position. In this embodiment, sheath 50a carries an inwardly extending annular projection 74, or a series of circumferentially disposed projections as an equivalent design. As sheath 50a is advanced forwardly relative to the hub and needle, annular projection 74 snaps into groove 70 in a snap-fit relation, to secure hub 14a and sheath 50a together.

The above has been offered for illustrative purposes only and is not intended to limit the scope of the invention of this application, which is as defined in the claims below.

Which is claimed:

1. A tubular medical needle set which comprises:

a needle and needle hub connected to an end of flexible tubing, plus a wing member positioned to facilitate manual gripping of said needle and hub, said wing member comprising a hub gripping portion carried by said needle hub in a generally fixed, axial position, and a wall portion attached to said hub gripping portion, said wall portion extending laterally outwardly from said hub gripping portion for manual gripping, said hub gripping portion being manually disengageable from said hub for manual removal of the wing member after said needle has been emplaced in a patient.

2. The set of claim 1, in which said wing member comprises a pair of walls and a hub gripping portion comprising attached hub gripping members gripping said hub, each attached hub gripping member being respectively positioned on opposed sides of the hub, with said pair of walls extending in generally parallel manner laterally outwardly each from one of said hub gripping members to define said wall portion, said walls being integrally attached together by a hinge wall, said walls each having a squeeze portion extending laterally outwardly beyond said hinge wall, whereby manual squeezing of said squeeze portion disengages said hub gripping members from the hub, to permit removal of the wing member.

3. The set of claim 2 which defines a groove extending at least partially around said needle hub, and said hub gripping members defining projections that fit in the groove, to restrict axial sliding of said wing member while gripping said hub.

4. The set of claim 3 in which said groove is defined between said hub and the connected, flexible tubing end.

5. A medical needle and needle hub connected to an end of flexible tubing, plus a substantially rigid tunnel member enclosing at least a portion of said hub, said tunnel member having a cross section of substantially the shape of an inverted U to define two tunnel edges for resting on the skin of a patient while the needle of the enclosed needle hub penetrates the patient's skin, said tunnel member having front and rear apertures through which said hub and tubing extend, the rear aperture being larger than the front aperture to accommodate a range of angular needle positions in the tunnel member.

6. The needle and hub of claim 5 with the tunnel member resting on the skin of a patient and enclosing at least a portion of said hub, the needle of said hub penetrating the patient's skin.

7. The needle and hub of claim 5 in which the front aperture of said tunnel member is at least in part defined by an inwardly extending flange, and a groove is defined at said hub that receives said flange, to prevent longitudinal movement between the tunnel member and hub.

8. The needle and hub of claim 7 in which said tunnel member is secured to the skin of a patient by a strip of medical tape and the needle penetrates the skin of said patient.

9. The method of obtaining needle access to the vascular system of a patient, which comprises: attaching a removable wing member to the hub of said needle in a manner to prevent substantially axial motion of said hub relative to the wing member; effecting needle access through the skin of the patient; removing the wing member from the hub; applying about the hub a tunnel member, said tunnel member having a cross section of substantially the shape of an inverted U to define two tunnel edges resting on the skin of a patient while the needle of the enclosed needle hub penetrates the patient's skin, said tunnel member providing longitudinal retention of said needle and needle hub while allowing axial rotatability to said needle and needle hub; and temporarily securing said tunnel member to the skin of the patient.

10. The method of claim 9, in which said tunnel member has front and rear apertures through which said needle hub and attached tubing extend, the rear aperture being larger than the front aperture to accommodate a range of angular needle positions of the needle hub in the tunnel member.

11. A medical procedure kit for performing the process of claim 9, which medical procedure kit comprises said needle and hub, said tubing, said wing member, and said tunnel member incorporated in a package with instructions for use.

* * * * *